US012672810B2

(12) United States Patent
    Smith

(10) Patent No.: US 12,672,810 B2
(45) Date of Patent: Jul. 7, 2026

(54) APPARATUS FOR MEASURING PUSHES DURING LABOR

(71) Applicant: Forrest O. Smith, Pleasanton, CA (US)

(72) Inventor: Forrest O. Smith, Pleasanton, CA (US)

( * ) Notice: Subject to any disclaimer, the term of this patent is extended or adjusted under 35 U.S.C. 154(b) by 274 days.

(21) Appl. No.: 18/471,457

(22) Filed: Sep. 21, 2023

(65) Prior Publication Data

US 2025/0099002 A1 Mar. 27, 2025

(51) Int. Cl.
A61B 5/22 (2006.01)
A61B 5/00 (2006.01)

(52) U.S. Cl.
CPC ............ A61B 5/227 (2013.01); A61B 5/6852 (2013.01); A61B 5/6867 (2013.01); *A61B 2562/0247* (2013.01)

(58) Field of Classification Search
CPC ...... A61B 5/227; A61B 5/6852; A61B 5/6867
See application file for complete search history.

(56) References Cited

U.S. PATENT DOCUMENTS

| | | | | |
|---|---|---|---|---|
| 5,566,680 | A | * 10/1996 | Urion | A61B 5/035 |
| | | | | 600/561 |
| 10,080,520 | B2 | * 9/2018 | Blurton | A61B 5/4356 |
| 10,966,654 | B2 | * 4/2021 | Bartlett | A61H 19/44 |
| 2013/0018308 | A1 | * 1/2013 | Rao | A63B 71/0622 |
| | | | | 604/99.04 |
| 2016/0030083 | A1 | * 2/2016 | Blurton | A61B 17/42 |
| | | | | 606/121 |
| 2022/0133166 | A1 | * 5/2022 | Ghodsian | A61B 5/435 |
| | | | | 600/304 |
| 2023/0037389 | A1 | * 2/2023 | Zhou | A61B 5/4255 |

* cited by examiner

*Primary Examiner* — Daniel L Cerioni
(74) *Attorney, Agent, or Firm* — PEARL COHEN ZEDEK LATZER BARATZ LLP

(57) ABSTRACT

A device to accurately measure the strength or level of the voluntary pushes supplied by the laboring mother during the second stage of labor through the contraction of her abdominal musculature, that comprises a hollow handheld base with a central lumen and a recess enclosing a calibrated spring into which a shaft with a central lumen capped by a mushroom-shaped outer surface is inserted which tip is applied to the anus to pass a catheter containing a solid-state pressure transducer to provide an accurate measure of the strength of voluntary maternal expulsive efforts without interfering with those efforts or with the birth canal of the mother.

20 Claims, 10 Drawing Sheets

Section A-A

Section B-B

Section B-B

FIG. 10 applying the mushroom-shaped tip to an external anus of a laboring mother

Figure 10:
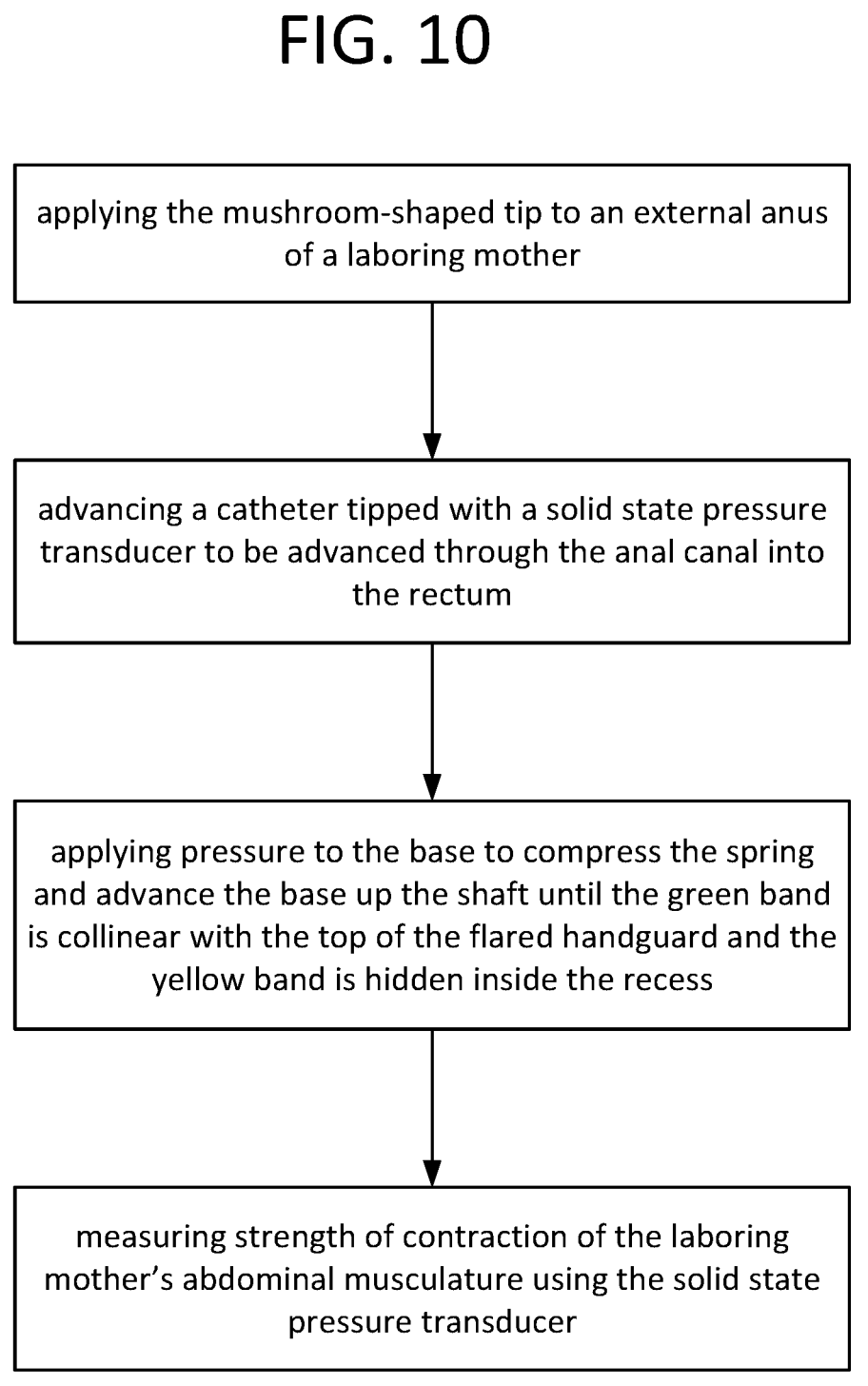

↓ advancing a catheter tipped with a solid state pressure transducer to be advanced through the anal canal into the rectum

↓ applying pressure to the base to compress the spring and advance the base up the shaft until the green band is collinear with the top of the flared handguard and the yellow band is hidden inside the recess

↓ measuring strength of contraction of the laboring mother's abdominal musculature using the solid state pressure transducer

APPARATUS FOR MEASURING PUSHES DURING LABOR

BACKGROUND

This disclosure relates in general to a method and system for use in the field of obstetrics (aka labor and delivery) for measurement of the strength of the maternal voluntary "pushes" in the second stage of human labor by a number of calibrated systems herein described.

It is of critical importance that in the second stage of human labor, defined as complete dilatation of the cervix to birth, the laboring mother augment the expulsive force already provided by the contractions of the uterine muscle with voluntary contractions of her abdominal musculature in the so-called Valsalva maneuver. Failure of the laboring mother to provide adequate expulsive force in the form of voluntary "pushes" is a frequent reason for the failure of vaginal delivery and the need for operative abdominal delivery (aka Cesarean section).

Although the strength of the uterine contractions can be measured and documented with the uterine contraction monitors commercially supplied and mounted on the mother's abdomen over the uterus, currently there is no device, meter, instrument or modality capable of accurate measurement of the strength or adequacy of the laboring mother's voluntary "pushes" (aka Valsalva Maneuver), leaving the Labor and Delivery staff to rely on the subjective perceptions of the laboring mother herself as well as those of the Delivery Team of doctors, nurses, physician associates, and midwives, as well of those of the laboring mother's support personnel in the form of family and/or friends.

BRIEF DESCRIPTION OF THE DRAWINGS

FIG. 10 is a flow chart describing operation of the proposed device.

DETAILED DESCRIPTION

The proposed device, depicted in FIGS. 1-9, accurately measures the strength or level of the voluntary pushes supplied by the laboring mother during the second stage of labor through the contraction of her abdominal musculature. The device comprises a handheld base (#2) topped with a flared handguard (#4) containing a recess (#20) enclosing a calibrated spring (#12) into which a shaft (#10) topped by a mushroom-shaped tip (#1) is inserted. Both base (#2) and tip (#1) contain a central lumen (#22) through which a flexible catheter (#30) tipped with a solid-state pressure transducer (#32) is passed and attached through a connector (#34) to an external pressure control unit (#24). The base (#2) is held by an operator labor attendant or doula with the tip (#1) applied to the anus of the laboring mother to allow the catheter (#30) tipped with solid-state pressure transducer (#32) to be advanced through the anal canal into the rectum. Catheter (#30) is connected through a standard off-the-shelf fitting (#34) to an external pressure control unit (#24) to document an accurate measure of the strength of voluntary contractions of the abdominal muscles (aka Valsalva maneuver) of the laboring mother to expel the fetus for the purpose of providing her encouragement and feedback as to the strength of her expulsive efforts without interfering with those efforts or obstructing the outlet of the birth canal of the mother.

The proposed device consists of three parts: 1) an oblate, semi-spheroidal base (#2) with a recess (#20) containing a central lumen (#22) and topped with a flared handguard (#4) the part so shaped to shield and protect the hands of the operator from contact with the bodily fluids of the laboring mother; 2) a top component comprising a mushroom-shaped tip (#1) containing a central lumen (#22) and a hollow shaft (#10) positioned below the mushroom-shaped tip with the hollow shaft having outer surface encircled by three colored bands of yellow (#14), green (#16) and red (#18), the part anatomically shaped to fit snugly within the contour of the external anus and position the device to pass the catheter (#30) easily into the rectum of the laboring mother, and; 3) a spring (#12).

Figure 1:
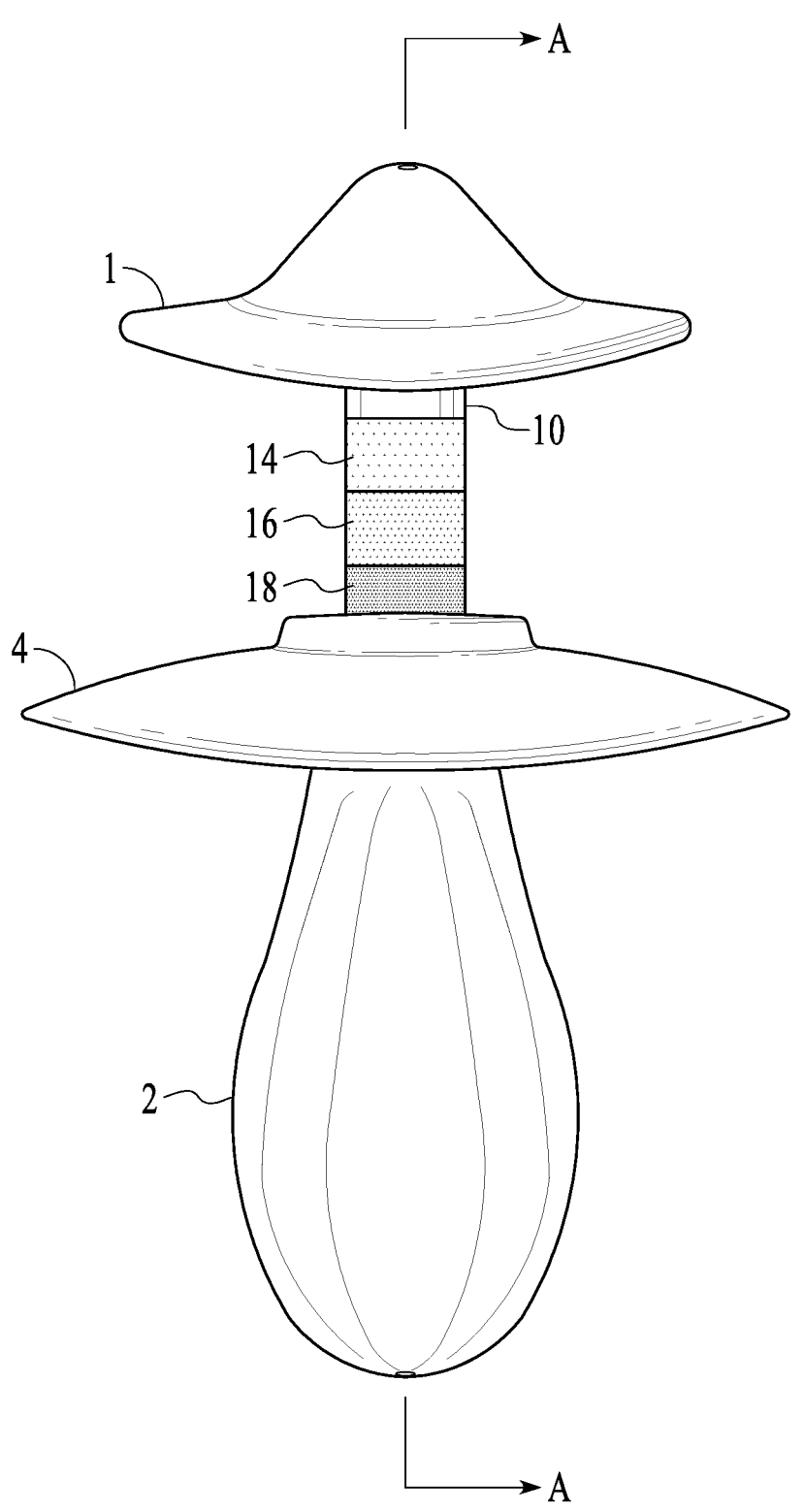
FIG. 1 shows the solid view of the assembled handheld device.

FIG. 1 shows the solid view of the assembled handheld device with the mushroom-shaped tip (#1) over the hollow shaft (#10) being inserted into the base (#2).

Figure 2:
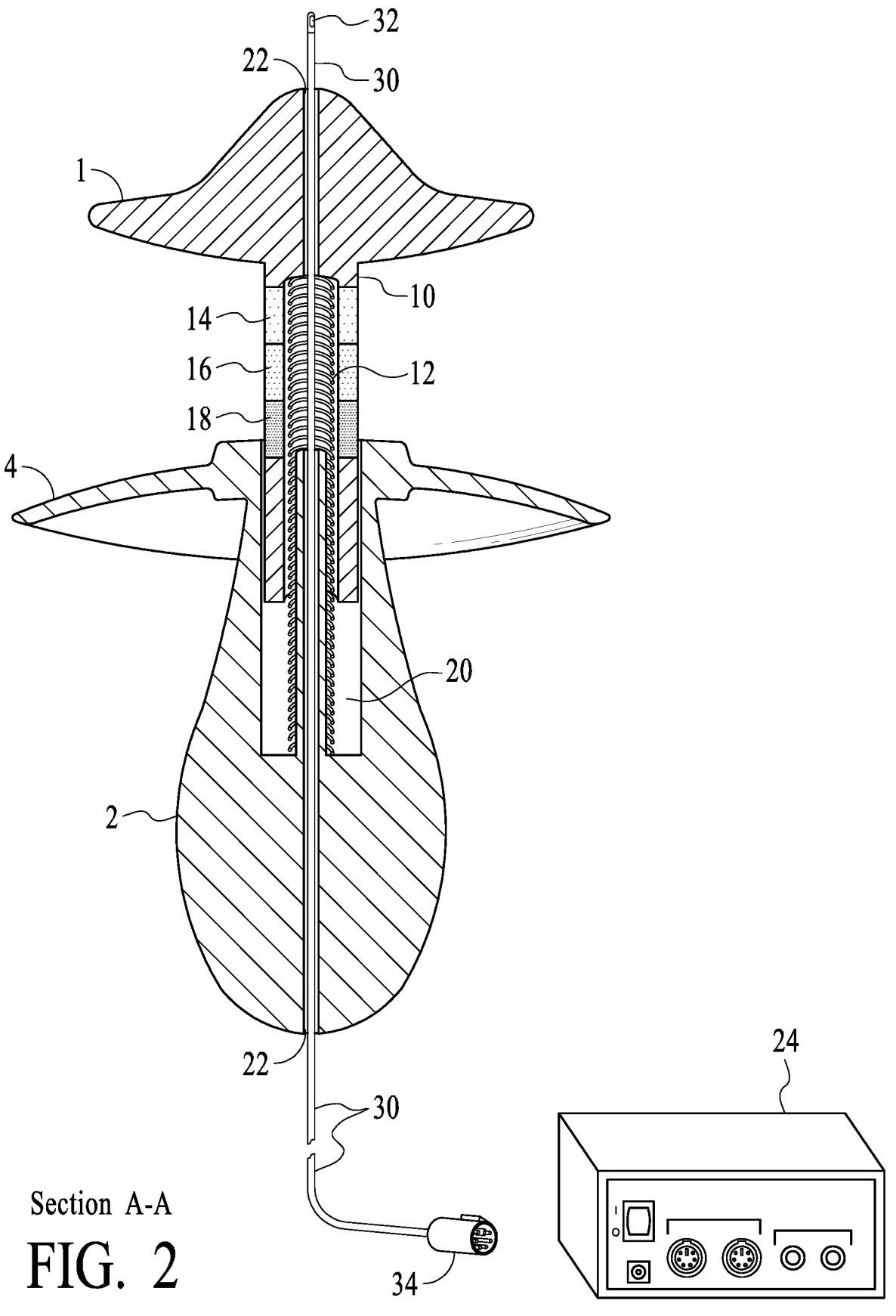
FIG. 2 is cutaway view of the device showing the lumen (#22) through which the solid-state pressure transducer catheter (#30) is passed and connected to an external pressure gauge control unit (#24).

FIG. 2 is a cutaway view of the device illustrating the mushroom-shaped tip (#1) on the shaft (#10) encircled by three colored bands of yellow (#14), green (#16) and red (#18) being inserted into the recess (#20) of the base (#2) and compressing the internal calibrated spring (#12) visible around the upward-projecting stem of the base (#2) with the configuration illustrated showing that when no pressure is applied and the position of the base (#2) on the shaft of with the mushroom-shaped tip (#1) is at the lowermost of the colored bands, (#18), the yellow one, indicating that insufficient pressure has been applied by the operator of the device to match the measured pressure inside the rectum.

FIG. 3 is again the solid view of the device, with the seemingly shortened shaft (#10) of the mushroom-shaped tip (#1) illustrating that pressure has been applied to compress the internal spring (#12) and advance the base (#2) partway up the shaft (#10) of the mushroom-shaped tip (#1) or, alternatively, pressure has been applied to result in the shaft (#10) of the mushroom-shaped tip (#1) retreating into the central recess (#20) of the base (#2) and compressing the internal spring (#12) but in both cases, sufficient pressure to show the top of the base (#2) at the level of the second of the colored bands on the shaft of the mushroom-shaped tip (#1), the green one, (#16) which position indicates correct pressure has been applied to match the measured pressure inside the rectum. In other words, the green band is collinear with the top of the flared handguard (#4).

Figure 3:
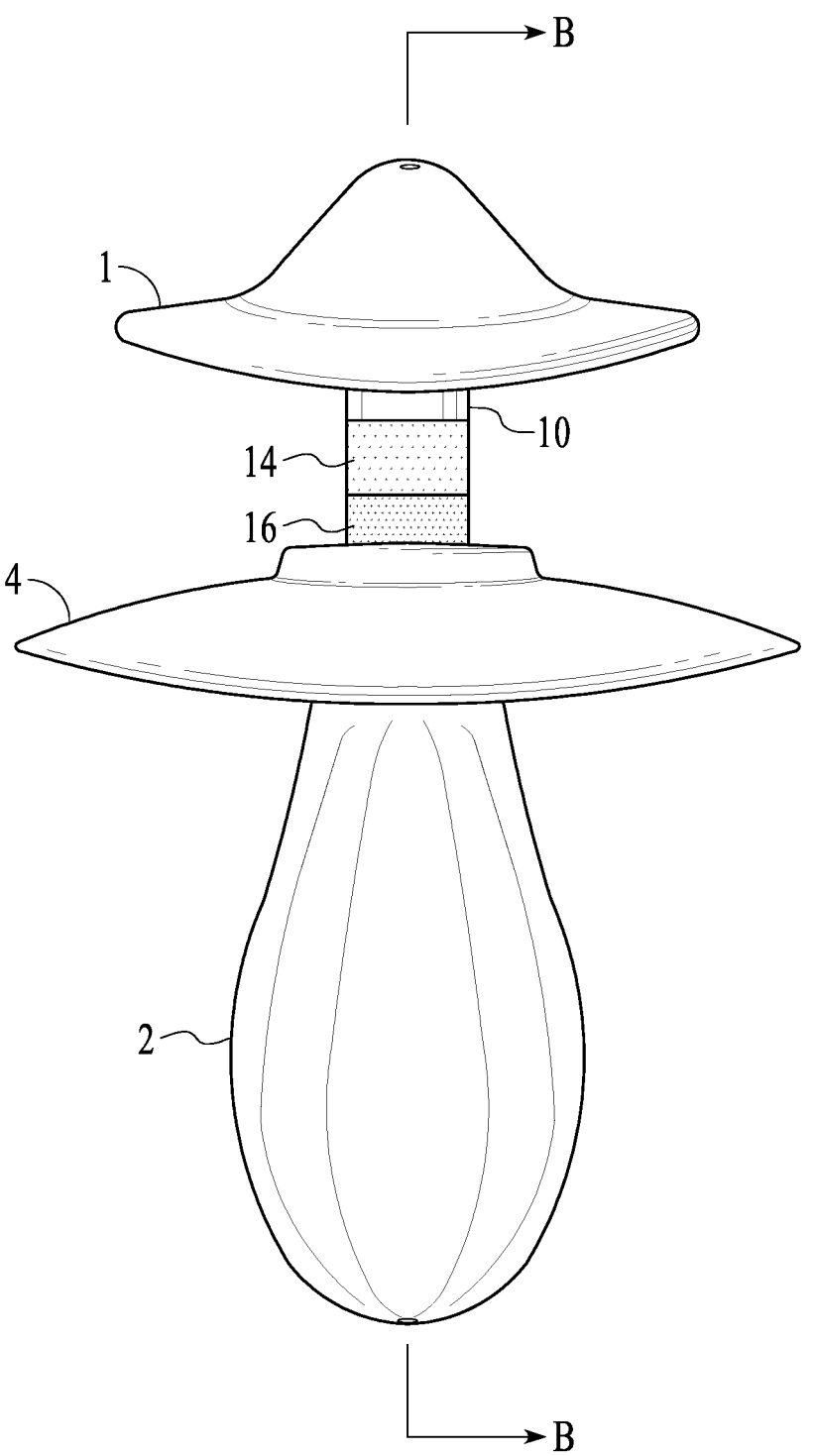
FIG. 3 is a solid view of the device.
Figure 4:
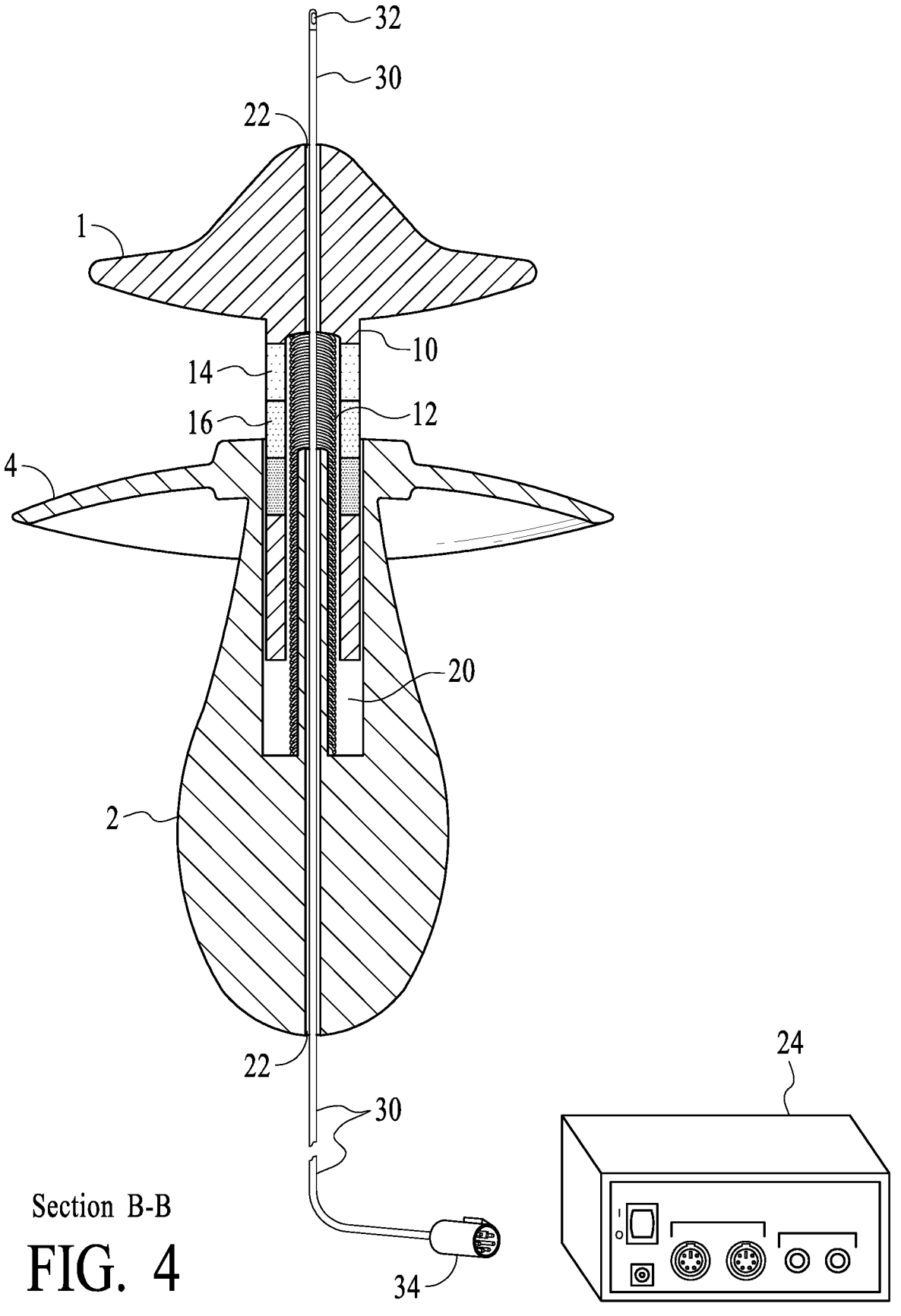
FIG. 4 is the cutaway view of the device as shown in FIG. 3 and showing the lumen (#22) through which the solid-state pressure transducer catheter (#30) is passed and connected to an external pressure gauge control unit (#24).

FIG. 4 is the cutaway view of the device as shown in FIG. 3, illustrating that pressure has been applied to advance the base (#2) partway up the shaft (#10) of the mushroom-shaped tip (#1) or, alternatively, pressure has been applied to result in the shaft (#10) of the mushroom-shaped tip (#1) retreating into the central recess (#20) of the base (#2) and compressing the internal spring (#12) but in both cases, sufficient pressure to show the top of the base (#2) at the level of the second of the colored bands on the shaft (#10) of the mushroom-shaped tip (#1), the green one, (#16) which position indicates correct pressure has been applied by the operator of the device to match the measured pressure inside the rectum.

Figure 5:
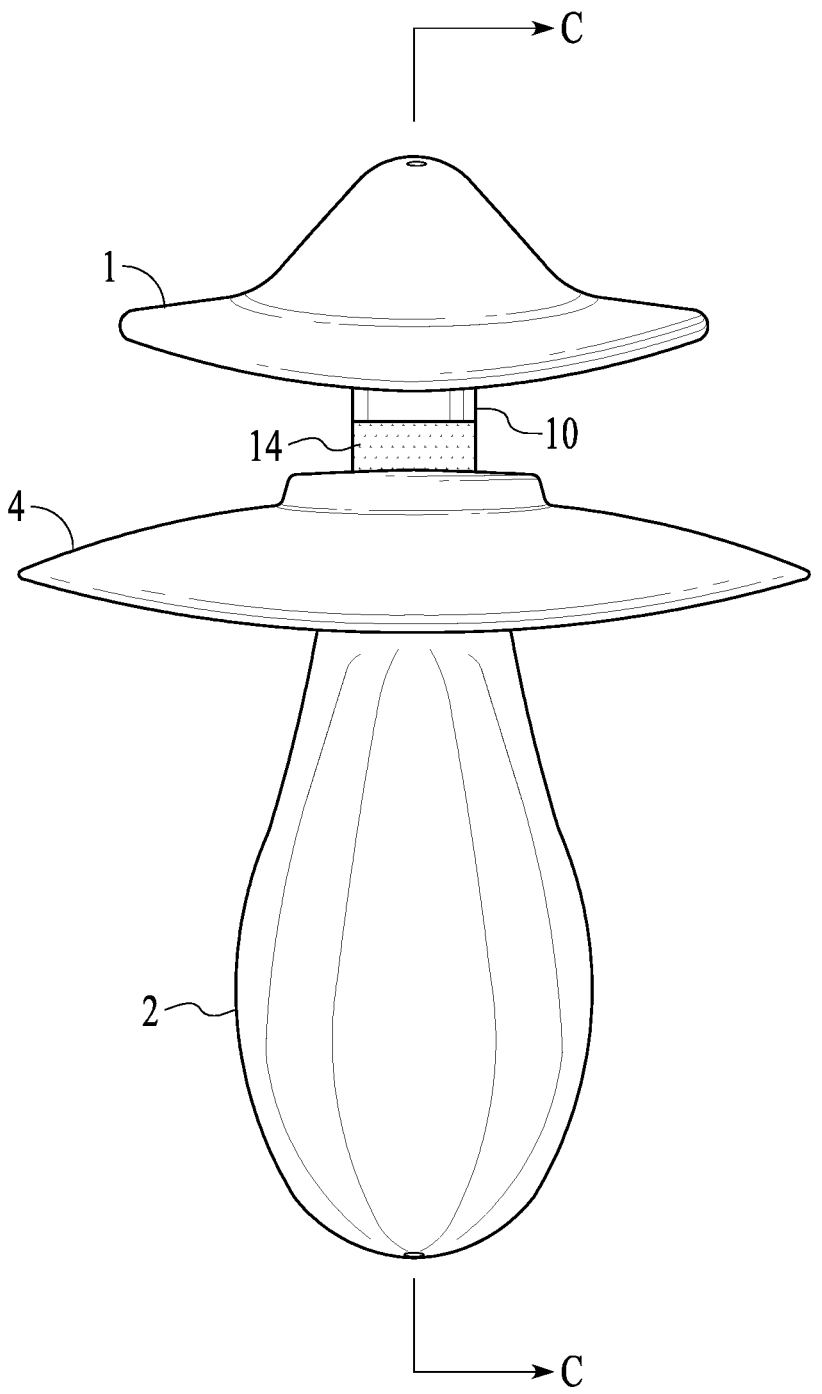
FIG. 5 is the solid view of the device illustrating the configuration when pressure is applied.

FIG. 5 is the solid view of the device illustrating that pressure has been applied to advance the base (#2) farther up the shaft of the mushroom-shaped tip (#1) or, alternatively, pressure has been applied to result in the shaft (#10) of the flared handguard tip (#1) further retreating into the central recess (#20) of the base (#2) and compressing the internal spring (#12) but in either case, sufficient pressure to show the top of the base (#2) at the level of the third of the colored bands on the shaft (#10) of the mushroom-shaped tip (#1), the red one, (#14), which position indicates pressure has been applied that exceeds the measured pressure inside the rectum.

Figure 6:
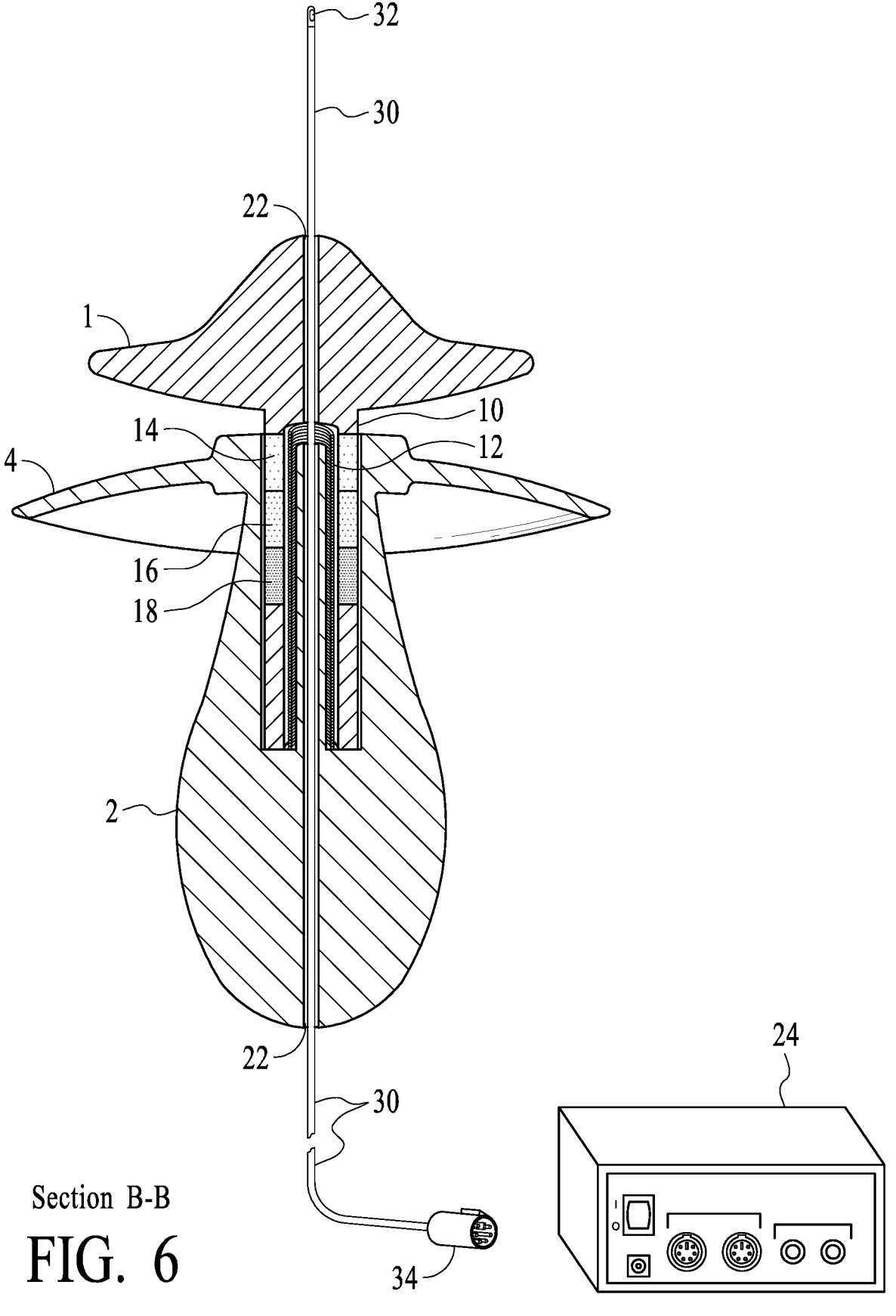
FIG. 6 is the cutaway view of the device in the same configuration as in FIG. 5 and showing the lumen (#22) through which the solid-state pressure transducer catheter (#30) is passed and connected to an external pressure gauge control unit (#24).

FIG. 6 is the cutaway view of the device in the same configuration as in FIG. 5, that is, illustrating the base (#2) as having advanced onto the shaft (#10) of the flared handguard tip (#1) or, alternatively, the shaft (#10) of the flared handguard tip (#1) as having retreated into the central recess (#20) of the base (#2) to the level of the uppermost of the colored bands on the shaft of the flared handguard tip (#1) which indicates an excessive amount of pressure has been applied by the operator of the device.

Figure 7:
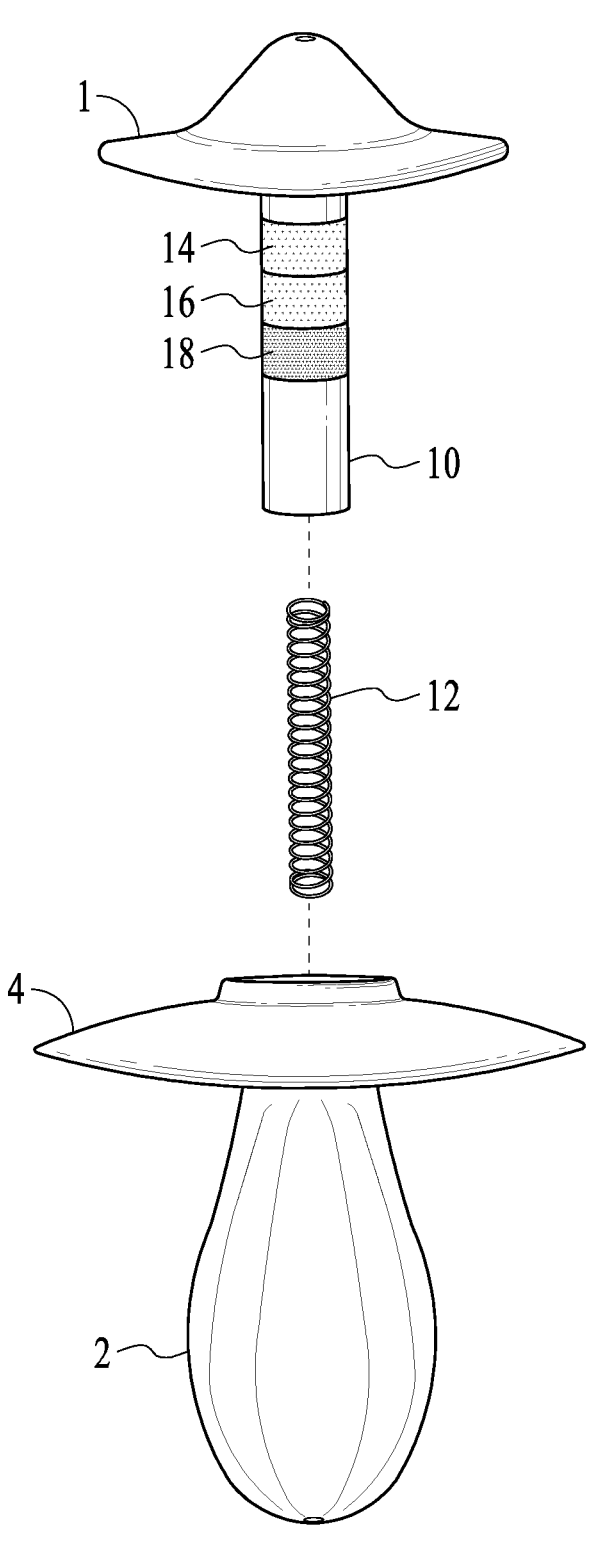
FIG. 7 shows an exploded view of the device.

FIG. 7 shows an exploded view of the three components of the device: the base (#2) topped by the flared handguard (#4), the calibrated spring (#12) and the mushroom-shaped tip (#1) over the shaft (#10) encircled with three colored bands of red (#14), green (#16) and yellow (#14).

Figure 8:
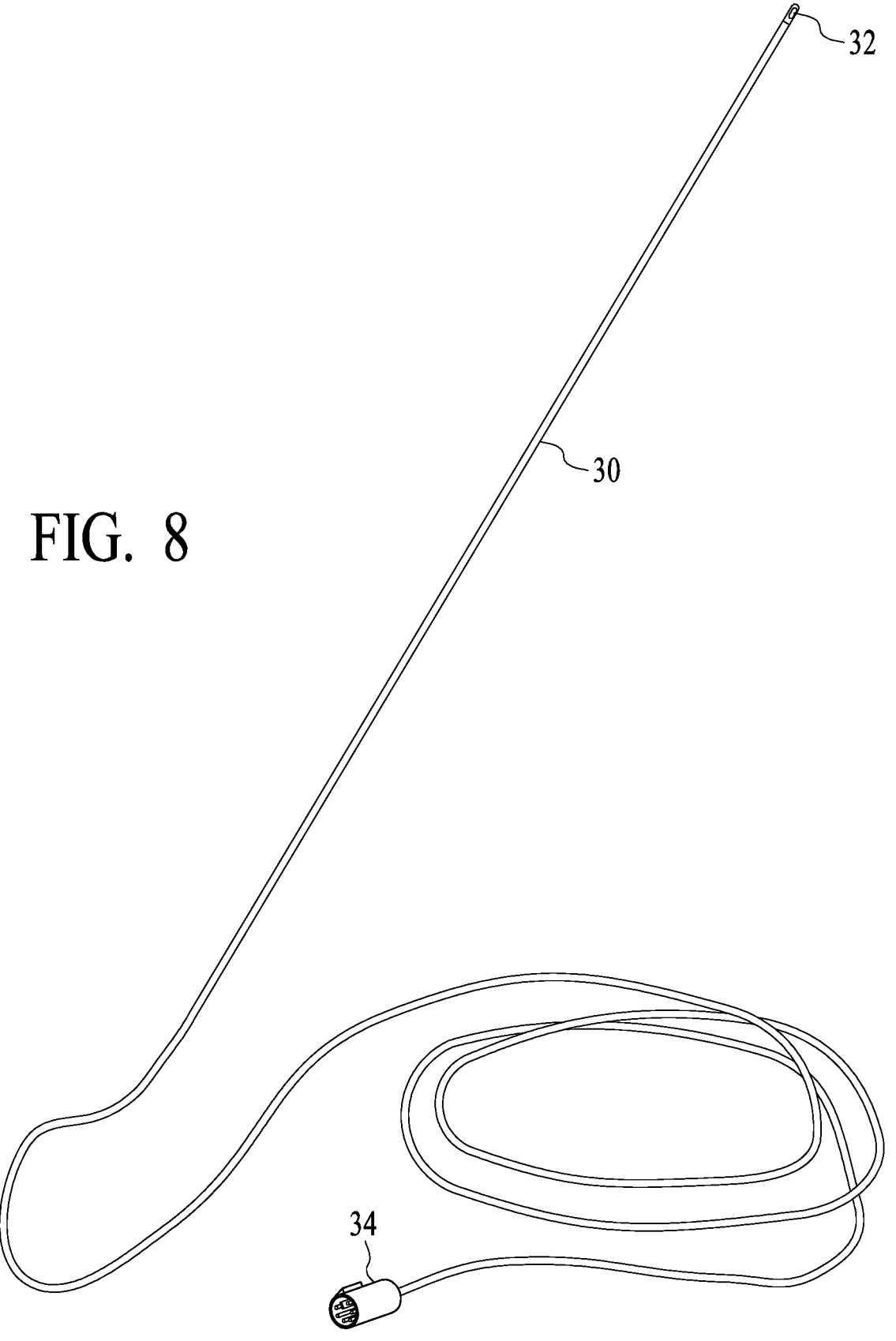
FIG. 8 shows the catheter (#30) tipped with a solid-state pressure transducer (#32) ending in the standard off-the-shelf fitting (#34).

FIG. 8 shows the catheter (#30) tipped with the solid-state pressure transducer (#32) and the fitting (#34) attached to the external pressure control unit (#24).

Figure 9:
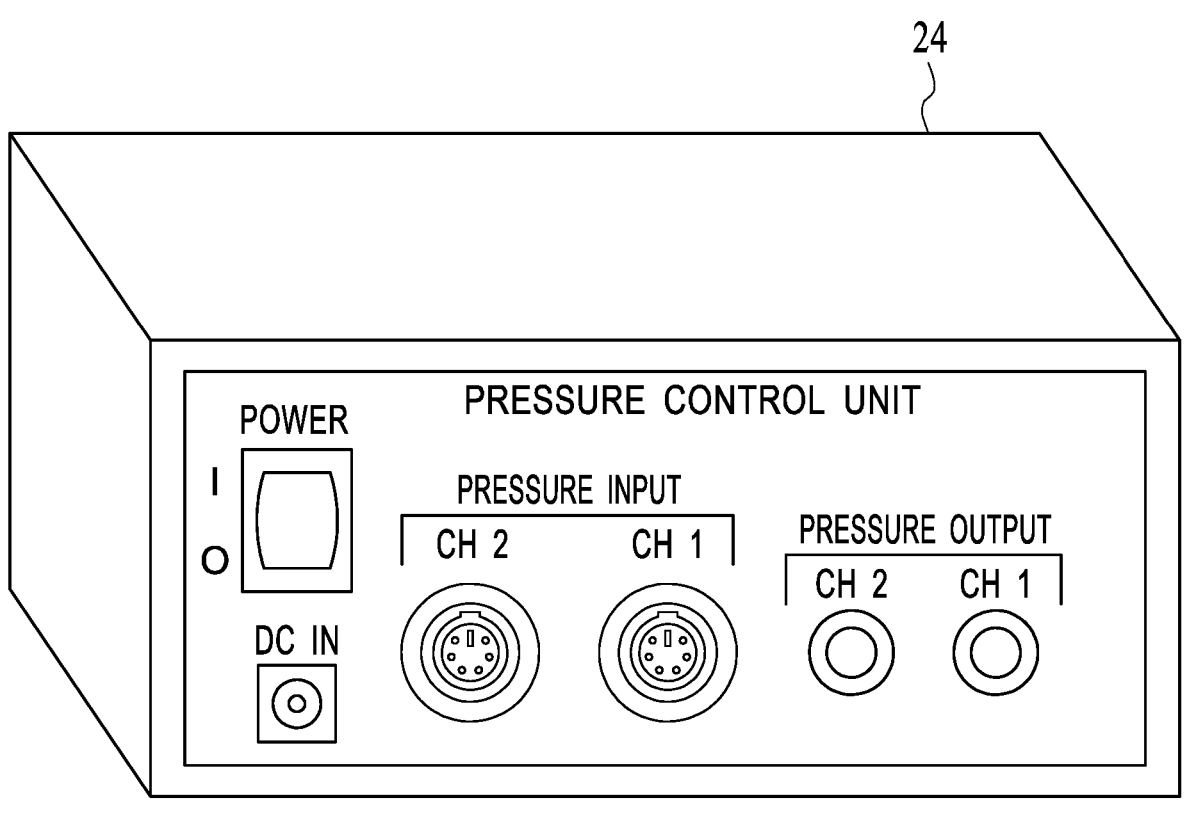
FIG. 9 shows the external pressure control unit (#24) to which the catheter (#30) is connected.

FIG. 9 shows the pressure control unit (#24) to which the solid-state internal pressure transducer (#32) is attached and which displays the pressure measured by the transducer (#32) inside the rectum of the laboring mother.

In one embodiment, the operator labor attendant or doula holds the device and applies the mushroom-shaped tip to the external anus and advances the catheter tipped by the solid-state pressure transducer (#32) through the anal canal and into the rectum to accurately measure the strength of expulsive efforts of the Valsalva Maneuver to coach and encourage the laboring mother in her voluntary efforts to effect birth in the second stage of labor.

In one embodiment, the operator holds the device and applies the bell-shaped tip to the external anus of the laboring mother and pushes forward to apply counterpressure and support to the anal sphincter to prevent overdistention and possible rupture.

In one embodiment, the operator holds the assembled device in hand and applies the mushroom-shaped tip (#1), to the external anus of the laboring mother and gently advances the catheter (#30) tipped with the solid-state pressure transducer (#32) inside the rectum to allow the external pressure control unit (#24) to accurately measure the pressure generated by the pushes of the laboring mother then applies pressure, which will result in the shaft (#10) of the mushroom-shaped tip retreating into the recess (#20) of the base (#2) or more accurately from the mechanical view, the base (#2) advancing up the shaft (#10) and compressing the internal spring (#12) which is so calibrated that the position of the base (#2) on the colored bands on the shaft (#10) allows the operator to accurately match the external counter-pressure exerted to the intra-rectal pressure as displayed by the pressure control unit (#24), with the yellow band (#18) generally indicating insufficient counter-pressure, the red band (#14) indicating excess counter-pressure and the green band (#16) indicating sufficient counter-pressure the purpose of the counter-pressure exerted by the labor attendant being two-fold, to support and protect the anus from breaking down from overdistension, and also to flatten the veins of the hemorrhoidal plexus to protect them from overdistension and decrease the incidence of post-partum hemorrhoids.

FIG. 10 is a flow chart describing operation of the proposed device disclosed in FIGS. 1-9. Step 102 includes applying the mushroom-shaped tip (#1) to an external anus of a laboring mother. Step 104 includes advancing catheter tipped with a solid state pressure transducer (#32) to be advanced through the anal canal into the rectum. Step 106 includes applying pressure to the base (#2) to compress the spring (#12) and advance the base (#2) up the shaft until the green band (#16) is collinear with the top of the flared handguard (#4) and the yellow band is hidden inside the recess, as depicted in FIG. 3. Step 108 includes measuring strength of contraction of the laboring mother's abdominal musculature using the solid state pressure transducer (#32).

In one exemplary aspect, the present disclosure is directed to a hand-held spring-loaded device which is applied to the external anus to provide passage of a solid-state pressure transducer into the rectum of the laboring mother and measure the force of her voluntary "pushes" for the purpose of giving her more accurate and helpful feedback as to the adequacy of the strength of her voluntary pushes and specifically to allow her to correlate her subjective feeling of the strength of her pushes with the accurately-measured strength as recorded by the solid-state pressure transducer, the intent being that she neither waste her energy on inadequate pushes nor exhaust it on excessive pushes.

In another exemplary aspect, the present disclosure is directed to a method of measuring the strength or force of the voluntary "pushes" of the laboring mother in the second stage of labor with a pneumatic tube within the stem with the strength of the voluntary contractions of the laboring mother aka Valsalva maneuver being accurately measured by the compression of the fluid or gas within the tube.

In another exemplary aspect, the device includes a hand-held base with a stem incorporating a pneumatic tube to measure the strength or force of the voluntary "pushes" of the laboring mother in the second stage of labor.

In another exemplary aspect, the device includes a stem incorporating a fluid-filled tube which compresses with the pressure of the force applied to measure the strength or force of the voluntary "pushes" of the laboring mother in the second stage of labor.

In another exemplary aspect, the device includes a stem incorporating an internal mechanical strain gauge which deforms with the pressure of the force applied to measure the strength or force of the voluntary "pushes" of the laboring mother in the second stage of labor.

One embodiment includes an apparatus to measure strength of voluntary pushes supplied by a laboring mother during a second stage of labor through the contraction of the laboring mother's abdominal musculature, comprising: a top component comprising a tip containing a central lumen and a hollow shaft positioned below the tip, the hollow shaft includes an outer surface with position indicators; a spring;

a base having a recess with an upward-projecting stem in the recess, the hollow shaft is positioned in the recess around the upward-projecting stem, the spring is positioned in the recess around the upward-projecting stem and inside the hollow shaft, the base and tip include a central lumen; a catheter positioned in the central lumen of the base and the tip; and a pressure transducer positioned at the tip of the catheter.

In one example implementation, the tip is a mushroom-shaped tip.

In one example implementation, the mushroom-shaped tip is anatomically shaped to fit snugly within the contour of an external anus.

In one example implementation, the position indicators include colored bands encircling the hollow shaft.

In one example implementation, the position indicators include three colored bands of yellow, green and red encircling the hollow shaft.

In one example implementation, the green band being collinear with the top of the flared handguard and the yellow band being hidden inside the recess indicates correct pressure has been applied to the base to match the measured pressure inside the rectum; the yellow band being collinear with the top of the flared handguard indicates insufficient pressure has been applied to the base that does not match the measured pressure inside the rectum; and the red band being collinear with the top of the flared handguard and the green band being hidden inside the recess indicates too much pressure has been applied to the base that does not match the measured pressure inside the rectum.

In one example implementation, the spring is a calibrated spring.

In one example implementation, the base is a semi-spheroidal base.

In one example implementation, the base is topped with a flared handguard to shield and protect a hand of an operator from contact with bodily fluids of the laboring mother.

In one example implementation, the pressure transducer is a solid state pressure transducer.

One example implementation further comprises a control unit connected to the catheter and in communication with the pressure transducer.

One example implementation further comprises an external pressure control unit connected to the catheter and in communication with the pressure transducer.

In one example implementation, the catheter is a flexible catheter.

In one example implementation, the base is a semi-spheroidal base; and the base is topped with a flared handguard to shield and protect a hand of an operator from contact with bodily fluids of the laboring mother.

In one example implementation, the tip is a mushroom-shaped tip; the base is a semi-spheroidal base; and the base is topped with a flared handguard to shield and protect a hand of an operator from contact with bodily fluids of the laboring mother.

In one example implementation, the position indicators include three colored bands of yellow, green and red encircling the hollow shaft; the green band being collinear with the top of the flared handguard and the yellow band being hidden inside the recess indicates correct pressure has been applied to the base to match the measured pressure inside the rectum; the yellow band being collinear with the top of the flared handguard indicates insufficient pressure has been applied to the base that does not match the measured pressure inside the rectum; and the red band being collinear with the top of the flared handguard and the green band being hidden inside the recess indicates too much pressure has been applied to the base that does not match the measured pressure inside the rectum.

One embodiment includes a method of measuring strength of voluntary pushes supplied by a laboring mother during a second stage of labor using an apparatus comprising: a top component comprising a mushroom-shaped tip containing a central lumen and a hollow shaft positioned below the mushroom-shaped tip, the mushroom-shaped tip is anatomically shaped to fit snugly within the contour of an external anus, the hollow shaft includes an outer surface encircled with three colored bands of yellow, green and red; a calibrated spring; a base having a recess with an upward-projecting stem in the recess and topped with a flared handguard the hollow shaft is positioned in the recess around the upward-projecting stem, the spring is positioned in the recess around the upward-projecting stem and inside the hollow shaft, the base and the mushroom-shaped tip include a central lumen; a flexible catheter positioned in the central lumen of the base and the mushroom-shaped tip; a solid state pressure transducer positioned at the tip of the catheter; and an external pressure control unit connected to the catheter and in communication with the solid state pressure transducer. The method comprises applying the mushroom-shaped tip to an external anus of a laboring mother; advancing catheter tipped with a solid state pressure transducer to be advanced through the anal canal into the rectum; applying pressure to the base to compress the spring and advance the base up the shaft until the green band is collinear with the top of the flared handguard and the yellow band is hidden inside the recess; and measuring strength of contraction of the laboring mother's abdominal musculature using the solid state pressure transducer.

In one example implementation, the applying pressure comprises pushes forward on the base to apply counterpressure and support to the anal sphincter to prevent overdistention and possible rupture.

In one example implementation, the applying pressure comprises the shaft of the mushroom-shaped tip retreating into the recess of the base and compressing the internal spring which is so calibrated that the position of the base on the colored bands on the shaft allows the operator to accurately match the external counter-pressure exerted to the intra-rectal pressure when the green band is collinear with the top of the flared handguard.

One embodiment includes an apparatus to accurately measure the strength of voluntary pushes supplied by a laboring mother during a second stage of labor through the contraction of the laboring mother's abdominal musculature, comprising: a top component comprising a mushroom-shaped tip containing a central lumen and a hollow shaft positioned below the mushroom-shaped tip, the mushroom-shaped tip is anatomically shaped to fit snugly within the contour of an external anus, the hollow shaft includes an outer surface encircled with three colored bands of yellow, green and red; a calibrated spring; an oblate, semi-spheroidal base having a recess with an upward-projecting stem in the recess and topped with a flared handguard to shield and protect a hand of an operator from contact with bodily fluids of the laboring mother, the hollow shaft is positioned in the recess around the upward-projecting stem, the spring is positioned in the recess around the upward-projecting stem and inside the hollow shaft, the base and the mushroom-shaped tip include a central lumen; a flexible catheter positioned in the central lumen of the base and the mushroom-shaped tip; a solid state pressure transducer positioned at the tip of the catheter; and an external pressure control unit connected to the catheter and in communication with the solid state pressure transducer.

For purposes of this document, reference in the specification to "an embodiment," "one embodiment," "some embodiments," or "another embodiment" may be used to describe different embodiments or the same embodiment.

For purposes of this document, a connection may be a direct connection or an indirect connection (e.g., via one or more other parts). In some cases, when an element is referred to as being connected or coupled to another element, the element may be directly connected to the other element or indirectly connected to the other element via one or more intervening elements. When an element is referred to as being directly connected to another element, then there are no intervening elements between the element and the other element. Two devices are "in communication" if they are directly or indirectly connected so that they can communicate electronic signals between them.

For purposes of this document, the term "based on" may be read as "based at least in part on."

For purposes of this document, without additional context, use of numerical terms such as a "first" object, a "second" object, and a "third" object may not imply an ordering of objects, but may instead be used for identification purposes to identify different objects.

For purposes of this document, the term "set" of objects may refer to a "set" of one or more of the objects.

The foregoing detailed description has been presented for purposes of illustration and description. It is not intended to be exhaustive or to limit to the precise form disclosed. Many modifications and variations are possible in light of the above teaching. The described embodiments were chosen in order to best explain the principles of the proposed technology and its practical application, to thereby enable others skilled in the art to best utilize it in various embodiments and with various modifications as are suited to the particular use contemplated. It is intended that the scope be defined by the claims appended hereto.

What is claimed is:

1. An apparatus to measure strength of voluntary pushes supplied by a laboring mother during a second stage of labor through a contraction of the laboring mother's abdominal musculature, comprising:
   a top component comprising a tip and a hollow shaft positioned below the tip, the hollow shaft includes an outer surface with position indicators;
   a spring;
   a base including a recess with an upward-projecting stem in the recess, the hollow shaft is positioned in the recess around the upward-projecting stem, the spring is positioned in the recess around the upward-projecting stem and inside the hollow shaft, a central lumen rums through the base and the tip;
   a catheter positioned in the central lumen of passing through the base and the tip; and
   a pressure transducer positioned at a first end of the catheter.

2. The apparatus of claim 1, wherein:
the tip is a mushroom-shaped tip.

3. The apparatus of claim 2, wherein:
the mushroom-shaped tip is anatomically shaped to fit snugly within a contour of an external anus.

4. The apparatus of claim 1, wherein:
the position indicators include colored bands encircling the hollow shaft.

5. The apparatus of claim 1, wherein:
the position indicators include three colored bands of yellow, green and red encircling the hollow shaft.

6. The apparatus of claim 5, wherein:
the base is topped with a flared handguard to shield and protect a hand of an operator from contact with bodily fluids of the laboring mother;
the green band being collinear with a top of the flared handguard and the yellow band being hidden inside the recess indicates correct pressure has been applied to the base to match the measured pressure inside a rectum;
the yellow band being collinear with the top of the flared handguard indicates insufficient pressure has been applied to the base that does not match a measured pressure inside the rectum; and
the red band being collinear with the top of the flared handguard and the green band being hidden inside the recess indicates too much pressure has been applied to the base that does not match the measured pressure inside the rectum.

7. The apparatus of claim 1, wherein:
the spring is a calibrated spring.

8. The apparatus of claim 1, wherein:
the base is a semi-spheroidal base.

9. The apparatus of claim 1, wherein:
the base is topped with a flared handguard to shield and protect a hand of an operator from contact with bodily fluids of the laboring mother.

10. The apparatus of claim 1, wherein:
the pressure transducer is a solid-state pressure transducer.

11. The apparatus of claim 1, further comprising:
a control unit connected to the catheter and in communication with the pressure transducer.

12. The apparatus of claim 1, further comprising:
an external pressure control unit connected to the catheter and in communication with the pressure transducer.

13. The apparatus of claim 1, wherein:
the catheter is a flexible catheter.

14. The apparatus of claim 1, wherein:
the base is a semi-spheroidal base; and
the base is topped with a flared handguard to shield and protect a hand of an operator from contact with bodily fluids of the laboring mother.

15. The apparatus of claim 1, wherein:
the tip is a mushroom-shaped tip;
the base is a semi-spheroidal base; and
the base is topped with a flared handguard to shield and protect a hand of an operator from contact with bodily fluids of the laboring mother.

16. The apparatus of claim 15, wherein:
the position indicators include three colored bands of yellow, green and red encircling the hollow shaft;
the green band being collinear a the top of the flared handguard and the yellow band being hidden inside the recess indicates correct pressure has been applied to the base to match the measured pressure inside a rectum;
the yellow band being collinear with the top of the flared handguard indicates insufficient pressure has been applied to the base that does not match the measured pressure inside the rectum; and
the red band being collinear with the top of the flared handguard and the green band being hidden inside the recess indicates too much pressure has been applied to the base that does not match the measured pressure inside the rectum.

17. A method of measuring strength of voluntary pushes supplied by a laboring mother during a second stage of labor using an apparatus comprising:

a top component comprising a mushroom-shaped tip and a hollow shaft positioned below the mushroom-shaped tip, the mushroom-shaped tip is anatomically shaped to fit snugly within a contour of an external anus, the hollow shaft includes an outer surface encircled with three colored bands of yellow, green and red;

a spring;

a base including a recess with an upward-projecting stem in the recess and topped with a flared handguard, the hollow shaft is positioned in the recess around the upward-projecting stem, the spring is positioned in the recess around the upward-projecting stem and inside the hollow shaft, a central lumen runs through the base and the mushroom-shaped tip;

a flexible catheter positioned in the central lumen passing through the base and the mushroom-shaped tip;

a solid-state pressure transducer positioned at a first end of the catheter; and an external pressure control unit connected to the catheter and in communication with the solid-state pressure transducer;

the method comprising:

applying the mushroom-shaped tip to an external anus of the laboring mother;

advancing the catheter with the solid-state pressure transducer through the anal canal into the rectum;

applying pressure to the base to compress the spring and advance the base up the shaft until the green band is collinear with a top of the flared handguard and the yellow band is hidden inside the recess; and measuring strength of contraction of the laboring mother's abdominal musculature using the solid-state pressure transducer.

18. The method of claim 17, wherein:

the applying pressure comprises pushes forward on the base to apply counterpressure and support to an anal sphincter to prevent overdistention and possible rupture.

19. The method of claim 17, wherein:

the applying pressure comprises the shaft of the mushroom-shaped tip retreating into the recess of the base and compressing the spring which is so calibrated that a position of the base on the colored bands on the shaft allows an operator to accurately match a external counter-pressure exerted to a intra-rectal pressure when the green band is collinear with the top of the flared handguard.

20. An apparatus to accurately measure the strength of voluntary pushes supplied by a laboring mother during a second stage of labor through the contraction of a laboring mother's abdominal musculature, comprising:

a top component comprising a mushroom-shaped tip and a hollow shaft positioned below the mushroom-shaped tip, the mushroom-shaped tip is anatomically shaped to fit snugly within a contour of an external anus, the hollow shaft includes an outer surface encircled with three colored bands of yellow, green and red;

a spring;

an oblate, semi-spheroidal base including a recess with an upward-projecting stem in the recess and topped with a flared handguard to shield and protect a hand of an operator from contact with bodily fluids of the laboring mother, the hollow shaft is positioned in the recess around the upward-projecting stem, the spring is positioned in the recess around the upward-projecting stem and inside the hollow shaft, a central lumen runs through the base and the mushroom-shaped tip;

a flexible catheter positioned in the central lumen passing through the base and the mushroom-shaped tip;

a solid-state pressure transducer positioned at a first end of the catheter; and an external pressure control unit connected to a second end of the catheter and in communication with the solid-state pressure transducer.

* * * * *